(12) United States Patent
Walker

(10) Patent No.: US 9,724,379 B2
(45) Date of Patent: Aug. 8, 2017

(54) THERAPEUTIC AGENTS WITH IMPROVED FIBRINOGEN BINDING

(75) Inventor: Greg Walker, Dunedin (NZ)

(73) Assignee: Haemostatix Limited, Nottinghamshire (GB)

( * ) Notice: Subject to any disclaimer, the term of this patent is extended or adjusted under 35 U.S.C. 154(b) by 0 days.

(21) Appl. No.: 13/983,031

(22) PCT Filed: Feb. 1, 2012

(86) PCT No.: PCT/GB2012/050217
§ 371 (c)(1),
(2), (4) Date: Oct. 3, 2013

(87) PCT Pub. No.: WO2012/104638
PCT Pub. Date: Aug. 9, 2012

(65) Prior Publication Data
US 2014/0031293 A1    Jan. 30, 2014

(30) Foreign Application Priority Data
Feb. 1, 2011  (GB) .................................. 1101740.7

(51) Int. Cl.
| | | |
|---|---|---|
| A61K 38/08 | (2006.01) | |
| C07K 17/00 | (2006.01) | |
| C07K 7/06 | (2006.01) | |
| A61K 47/48 | (2006.01) | |

(52) U.S. Cl.
CPC .......... *A61K 38/08* (2013.01); *A61K 47/4893* (2013.01); *A61K 47/48284* (2013.01); *A61K 47/48292* (2013.01); *A61K 47/48784* (2013.01); *A61K 47/48876* (2013.01); *C07K 7/06* (2013.01); *C07K 17/00* (2013.01)

(58) Field of Classification Search
CPC ........ A61K 38/08; A61K 39/02; A61K 38/00; A61K 47/4893; A61K 47/48784; A61K 47/48769; A61K 47/48246; A61K 47/48238; A61K 47/48007; A61K 47/00; C07K 2/00; C07K 7/04; C07K 7/00
See application file for complete search history.

(56) References Cited

U.S. PATENT DOCUMENTS

| | | | |
|---|---|---|---|
| 4,427,651 | A | 1/1984 | Stroetmann |
| 6,113,948 | A | 9/2000 | Heath et al. |
| 9,339,584 | B2 * | 5/2016 | Walker ................ A61L 24/0031 |
| 2006/0104970 | A1 | 5/2006 | Margel et al. |
| 2009/0075891 | A1 | 3/2009 | MacPhee et al. |

FOREIGN PATENT DOCUMENTS

| | | | |
|---|---|---|---|
| GB | 2 429 153 A | 2/2007 | |
| GB | WO 2008/065388 | * 6/2008 | ............. A61L 24/10 |
| WO | 92/18164 A1 | 10/1992 | |
| WO | 97/26280 A1 | 7/1997 | |
| WO | 98/17319 A3 | 4/1998 | |
| WO | 99/25383 A1 | 5/1999 | |
| WO | 2005/035002 A1 | 4/2005 | |
| WO | 2006/012541 A2 | 2/2006 | |
| WO | 2007/015107 A2 | 2/2007 | |
| WO | 2008/065388 A2 | 6/2008 | |
| WO | 2010/088469 A2 | 8/2010 | |
| WO | 2010/117694 A2 | 10/2010 | |

OTHER PUBLICATIONS

McNerny et al., Nanomedicine and Nanobiotechnology (2010) 2(3), 249-259.*
https://www.thermofisher.com/us/en/home/life-science/protein-biology/protein-biology-learning-center/protein-biology-resource-library/pierce-protein-methods/polyethylene-glycol-peg-pegylation-proteins.html , accessed online Oct. 16, 2016, 8 pages.*
Bennett, "Platelet-Fibrinogen Interactions," *Annals New York Academy of Sciences* 936:340-352, 2001.
Ellman, "Tissue Sulfhydryl Groups," *Archives of Biochemistry and Biophysics* 82:70-77, 1959.
Hermanson, "Bioconjugate Techniques," 2$^{nd}$ Ed., *Elsevier Inc.* 125:114-129, 2008.
Kommareddy et al., "Preparation and Evaluation of Thiol-Modified Gelatin Nanoparticles for Intracellular DNA Delivery in Response to Glutathione," *Bioconjugate Chem.* 16:1423-1432, 2005.
Mosesson et al., "The Structure and Biological Features of Fibrinogen and Fibrin," *Annals New York Academy of Sciences* 936:11-30, 2001.
Poschalko et al., "SUBPOL: A Novel Sucrose-Based Polymer Support for Solid-Phase Peptide Synthesis and Affinity Chromatography Applications," *J. Am. Chem. Soc.* 125(44):13415-13426, 2003.
Scheefers-Borchel et al., "Discrimination between fibrin and fibrinogen by a monoclonal antibody against a synthetic peptide," *Proc. Natl. Acad. Sci. USA* 82(20):7091-7095, Oct. 1985.
Thermo Scientific, "SM(PEG)$_n$ Cross linkers. Amine-to-sulfhydryl cross linkers with soluble polyethylene glycol (PEG) spacer arms," *Pierce Biotechnology*:1-5, Mar. 20, 2008.
Thermo Scientific, Intellectual Property Office, "Ethylenediamine dihydrochloride," www.ipo.gov.uk, retrieved on Nov. 5, 2013.
Xia et al., "Optimally functional fluorescein isothiocyanate-labelled fibrinogen for quantitative studies of binding to activated platelets and platelet aggregation," *British Journal Of Haematology* 93:204-214, 1996.
Haynie et al., "Antimicrobial Activities of Amphiphilic Peptides Covalently Bonded to a Water-Insoluble Resin," *Antimicrobial Agents and Chemotherapy* 39(2):301-307, 1995.

* cited by examiner

*Primary Examiner* — Marcela M Cordero Garcia
*Assistant Examiner* — Catherine Mader
(74) *Attorney, Agent, or Firm* — Seed IP Law Group LLP

(57) ABSTRACT

Therapeutic agents with improved fibrinogen binding properties are described. The agents are suitable for use as artificial platelets, or for formation of biogels. Methods and intermediates for producing the agents, cross-linking agents for use in the methods, and biogels formed from, or comprising the agents, are also described.

7 Claims, 3 Drawing Sheets

Figure 1:
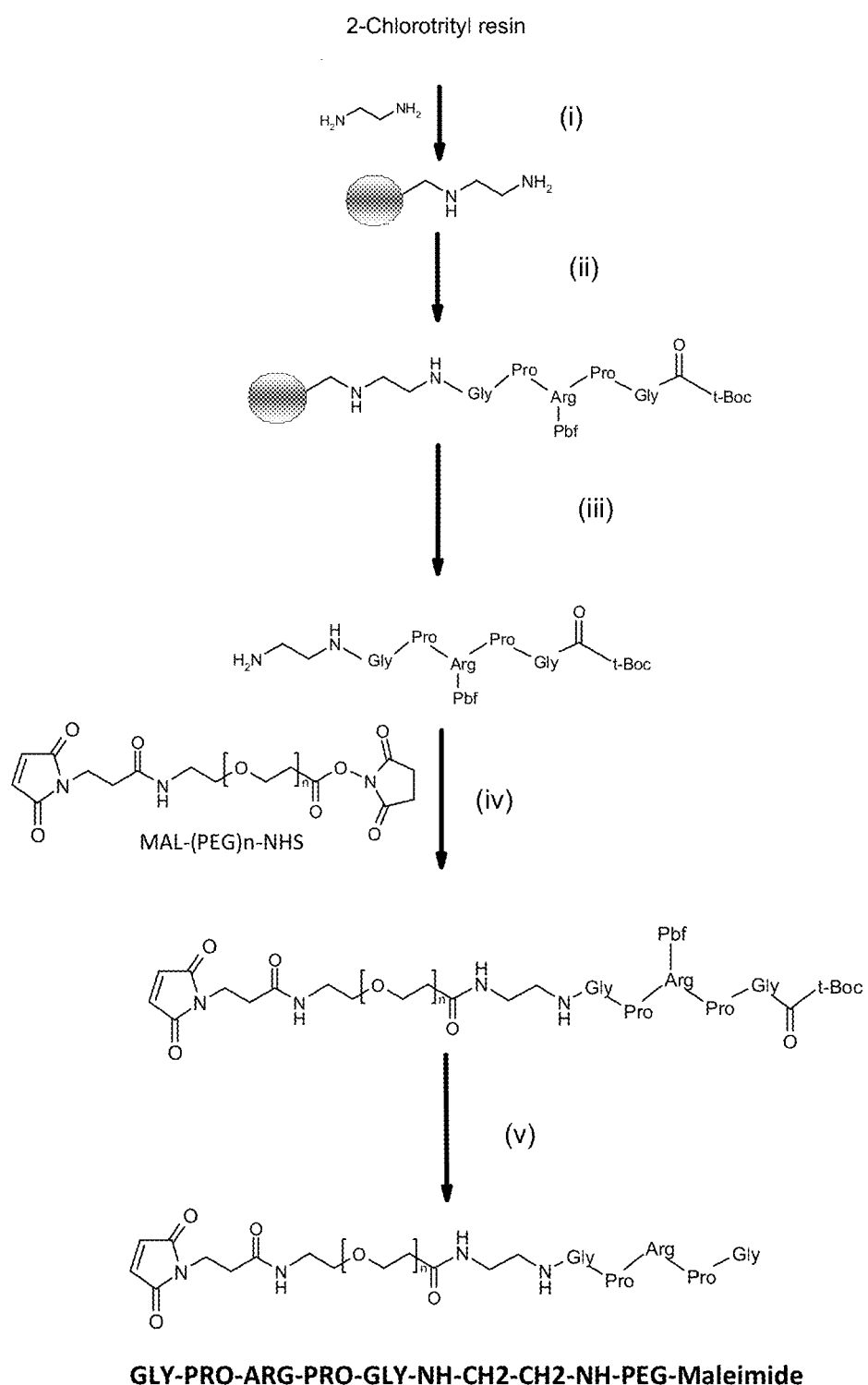

**GLY-PRO-ARG-PRO-GLY-NH-CH2-CH2-NH-PEG-Maleimide
(GPRPG-PEG-MAL)**

SEQUENCE LISTING

```
<160> NUMBER OF SEQ ID NOS: 11

<210> SEQ ID NO 1
<211> LENGTH: 11
<212> TYPE: PRT
<213> ORGANISM: Artificial
<220> FEATURE:
<223> OTHER INFORMATION: artificial peptide sequence

<400> SEQUENCE: 1

Gly Pro Arg Pro Gly Gly Gly Gly Gly Gly Cys
1               5                   10

<210> SEQ ID NO 2
<211> LENGTH: 4
<212> TYPE: PRT
<213> ORGANISM: Artificial
<220> FEATURE:
<223> OTHER INFORMATION: Artificial peptide sequence
<220> FEATURE:
<221> NAME/KEY: misc_feature
<222> LOCATION: (4)..(4)
<223> OTHER INFORMATION: any amino acid

<400> SEQUENCE: 2

Gly Pro Arg Xaa
1

<210> SEQ ID NO 3
<211> LENGTH: 4
<212> TYPE: PRT
<213> ORGANISM: Artificial
<220> FEATURE:
<223> OTHER INFORMATION: Artificial peptide sequence
<220> FEATURE:
<221> NAME/KEY: misc_feature
<222> LOCATION: (4)..(4)
<223> OTHER INFORMATION: any amino acid

<400> SEQUENCE: 3

Gly His Arg Xaa
1
```

```
<210> SEQ ID NO 4
<211> LENGTH: 5
<212> TYPE: PRT
<213> ORGANISM: Artificial
<220> FEATURE:
<223> OTHER INFORMATION: Artificial peptide sequence

<400> SEQUENCE: 4

Gly Pro Arg Pro Gly
1               5

<210> SEQ ID NO 5
<211> LENGTH: 8
<212> TYPE: PRT
<213> ORGANISM: Artificial
<220> FEATURE:
<223> OTHER INFORMATION: Artificial peptide sequence
<220> FEATURE:
<221> NAME/KEY: misc_feature
<222> LOCATION: (1)..(1)
<223> OTHER INFORMATION: any amino acid
<220> FEATURE:
<221> NAME/KEY: misc_feature
<222> LOCATION: (2)..(2)
<223> OTHER INFORMATION: any amino acid
<220> FEATURE:
<221> NAME/KEY: misc_feature
<222> LOCATION: (3)..(3)
<223> OTHER INFORMATION: any amino acid

<400> SEQUENCE: 5

Xaa Xaa Xaa Arg Gly Pro Arg Pro
1               5

<210> SEQ ID NO 6
<211> LENGTH: 8
<212> TYPE: PRT
<213> ORGANISM: Artificial
<220> FEATURE:
<223> OTHER INFORMATION: Artificial peptide sequence

<400> SEQUENCE: 6

Leu Val Pro Arg Gly Pro Arg Pro
1               5

<210> SEQ ID NO 7
<211> LENGTH: 8
<212> TYPE: PRT
<213> ORGANISM: Artificial
<220> FEATURE:
<223> OTHER INFORMATION: Artificial peptide sequence

<400> SEQUENCE: 7

Ala Asp Pro Arg Gly Pro Arg Pro
1               5

<210> SEQ ID NO 8
<211> LENGTH: 8
<212> TYPE: PRT
<213> ORGANISM: Artificial
<220> FEATURE:
<223> OTHER INFORMATION: Artificial peptide sequence

<400> SEQUENCE: 8

Leu Asp Pro Arg Gly Pro Arg Pro
1               5

<210> SEQ ID NO 9
<211> LENGTH: 8
```

```
<212> TYPE: PRT
<213> ORGANISM: Artificial
<220> FEATURE:
<223> OTHER INFORMATION: Artificial peptide sequence

<400> SEQUENCE: 9

Leu Val Pro Arg Gly Pro Arg Val
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic peptide

<400> SEQUENCE: 10

Gly Pro Arg Pro Lys
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic peptide spacer conjugate
<220> FEATURE:
<221> NAME/KEY: MOD_RES
<222> LOCATION: (5)...(5)
<223> OTHER INFORMATION: conjugated with PEG12-maleimide

<400> SEQUENCE: 11

Gly Pro Arg Pro Gly
1               5
```

THERAPEUTIC AGENTS WITH IMPROVED FIBRINOGEN BINDING

STATEMENT REGARDING SEQUENCE LISTING

The Sequence Listing associated with this application is provided in text format in lieu of a paper copy, and is hereby incorporated by reference into the specification. The name of the text file containing the Sequence Listing is 430160_404USPC_SEQUENCE_LISTING.txt. The text file is 2.7 KB, was created on Jul. 30, 2013, and is being submitted electronically via EFS-Web.

This invention relates to agents with improved fibrinogen binding properties. The agents are suitable for use as artificial platelets, or for formation of biogels. The invention also relates to methods and intermediates for producing such agents, to cross-linking agents for use in the methods, and to biogels formed from, or comprising the agents.

Platelet transfusion is currently the only effective treatment for acute bleeding and the prevention of bleeding in patients with disorders of platelet production and/or function. However, the shelf-life of platelet concentrates used for transfusion is only five days. There is also a risk of infection associated with platelet transfusion, and a risk that the patient may have an allergic reaction to platelet concentrates.

In view of the problems associated with platelet concentrates and platelet transfusion, attempts have been made to develop artificial platelets. WO 2005/035002 describes production of two artificial platelet products. Product 1 is a peptide of sequence $NH_2$-GPRPGGGGGGC (SEQ ID NO: 1) cross-linked through the terminal cysteine to a human albumin microsphere. Fibrinogen is bound to the peptide. Product 2 is identical to Product 1 except that fibrinogen is not bound to the peptide. When administered, Product 2 binds endogenous fibrinogen via the peptide. The peptide is capable of binding to fibrinogen such that fibrinogen is maintained in, or close to, its native conformation. This allows preferential interaction with the activated form of the GPIIb-IIIa receptor. The bound fibrinogen can also interact with thrombin, which cleaves fibrinogen, allowing cross-linking of the microspheres through fibrin-fibrin bridges.

WO 2007/015107 describes an agent comprising a fibrinogen binding precursor peptide bound to an insoluble carrier. The peptide can be cleaved by thrombin to expose a fibrinogen binding peptide bound to the carrier. The fibrinogen binding precursor peptide has low affinity for fibrinogen, and so the agent is only active at the site of a wound where thrombin is present. WO 2007/015107 describes (in Example 2) use of dithio-bis(2-nitrobenzoic acid) (DTNB) to couple the carboxy-terminal cysteine of a fibrinogen binding precursor peptide to a carrier composed of human albumin. The resulting product contains the peptide bound to the carrier by a disulphide bond. However, such bonds are less stable than other covalent bonds, and the process for formation of the disulphide bond is a two-step process. DTNB and the intermediate formed are potentially toxic, and may require removal during the production process.

WO 2007/015107 also describes (in Example 5) linking of a carboxy-terminal lysine of a fibrinogen binding precursor peptide to a carrier composed of human serum albumin. The peptide was synthesised with a maleimide moiety at the carboxy-terminus of the peptide. The maleimide was reacted with reactive groups on the carrier to immobilise the peptide to the carrier.

WO 2008/065388 describes (in Example 1) use of the cross linking agent succinimidyl-4-(N-maleimidomethyl) cyclohexane-1-carboxylate (SMCC) to couple the carboxy-terminal cysteine of a fibrinogen binding peptide or fibrinogen binding precursor peptide to a carrier composed of human albumin. The resulting product contains the peptide bound to the carrier by a linkage that includes a succinimide group and a cyclohexane group. The presence of cyclic groups is believed to increase the immunogenicity of the agent.

It is desired to provide agents for use as artificial platelets, or for the formation of biogels, that have improved fibrinogen binding properties. It is also desired to provide agents with reduced immunogenicity, and agents that can be produced without use of toxic reagents.

According to the invention, there is provided an agent, which comprises a carrier and a plurality of fibrinogen binding peptides, or fibrinogen binding precursor peptides, wherein each peptide is covalently immobilised to the carrier by a non-peptide spacer that is covalently linked directly to a main chain α-carbonyl group at a carboxy-terminal end of the peptide.

Agents of the invention have been found to bind more molecules of fibrinogen per carrier than agents in which the fibrinogen binding peptide is immobilized via a side chain of a carboxy-terminal amino acid of the peptide. The reason for the increased binding of agents of the invention to fibrinogen is not fully understood. However, it is believed that covalent linkage of the non-peptide spacer directly to the main chain α-carbonyl group at the carboxy-terminal end of the peptide may present the peptide in a more linear orientation away from the carrier than if a side chain of the carboxy-terminal residue is used, thereby increasing the accessibility of the fibrinogen binding peptide to fibrinogen. It is also believed that the negative charge from the free carboxy group that is present at the carboxy-terminal end of a peptide immobilised via a side chain of the carboxy-terminal residue could interfere electrostatically with binding to fibrinogen. There is no free carboxy group when the peptide is immobilised by linkage to the main chain α-carbonyl group.

Fibrinogen comprises two terminal domains (D-domains), each of which can bind to a fibrinogen-binding peptide. When fibrinogen, for example in plasma or blood, contacts the peptides, a copolymer is formed comprising the fibrinogen-binding peptides and fibrinogen which has characteristics of a fibrin clot.

Agents of the invention have good haemostatic properties. Example 5 below demonstrates that an agent of the invention forms visible clots in less than 6 seconds when mixed with fibrinogen. Example 6 shows that a different agent of the invention forms durable plugs when mixed with plasma.

Agents of the invention may be in dry form, or in solution or suspension. Agents of the invention can be stored long-term at room temperature in solution.

The term "non-peptide spacer" is used herein to include a spacer which does not have any amino acid residues. A tendency for the non peptide spacer to form intramolecular bonds may adversely affect presentation of the fibrinogen binding peptide or precursor peptide to fibrinogen. For example, formation of intramolecular bonds could cause the non-peptide spacer to fold in on itself such that the peptide is not optimally presented outwardly from the carrier. Consequently, in preferred embodiments, the non-peptide spacer has a low tendency to form intramolecular bonds.

The term "intramolecular bonds" as used herein includes hydrogen-bonds and salt bridges. This term also includes the hydrophobic interactions which occur when a molecule, such as a polypeptide, containing hydrophobic groups is placed in a polar solvent such as water and the hydrophobic groups tend to get buried in the interior of the molecule, away from water molecules.

Preferably the non-peptide spacer comprises a spacer group which is a hydrophilic group. Hydrophilic groups interact with surrounding water molecules and thereby discourage folding of the non-peptide spacer in on itself. Preferably, the hydrophilic group is at least 10, 20, 30, 40 or 50 Å in length. Preferably the hydrophilic group is up to 100 Å in length. According to a preferred embodiment, the hydrophilic group is 17.6 Å in length. Preferably, a non peptide spacer incorporating the hydrophilic group has a length of 20 to 100, 30 to 80, 40 to 70 or 50 to 60 Å.

In preferred embodiments the hydrophilic group is a straight chain group. The straight chain group should be non-toxic and flexible. Preferably the straight chain group comprises an ethylene oxide group, such as a polyethylene glycol (PEG) of formula —$(CH_2CH_2O)_x$—, where x is at least 1, 2, 4, 6, 8, 10 or 20. Preferably x is up to 50, for example, 1-50, preferably 2-24, more preferably 12.

The non-peptide spacer may include a first, non-peptide linker, which is covalently linked directly to the main chain α-carbonyl group of the peptide. Preferably the first linker is a straight chain linker. In a preferred embodiment, the first linker comprises the group —$(CH_2)_a$—, wherein a is 1-20, preferably 1-15, 1-10, 1-5, or 2-4. Preferably the first linker is covalently linked to the peptide by an amide bond in which the main chain α-carbonyl group at the carboxy-terminal end of the peptide is part of the amide bond. Preferably the first linker is covalently linked to the rest of the spacer by an amide bond. In a preferred embodiment, the first linker is formed by use of ethylene diamine.

The non-peptide spacer may include a second, non-peptide linker, which is covalently linked to the carrier.

In a preferred arrangement, an agent of the invention comprises the following general formula (I):

[Peptide-CO-A-X-B-]$_n$Carrier     (I)

Where:
"Peptide-CO" represents a fibrinogen binding peptide or fibrinogen binding precursor peptide and the main chain α-carbonyl group at the carboxy-terminal end of the peptide; "-A-X-B-" represents the non-peptide spacer, where A is a first linker of the non-peptide spacer covalently linked directly to the main chain α-carbonyl group of the peptide, X is a spacer group, and B is a second linker of the non-peptide spacer covalently linked to the carrier; and n is >1, and so indicates that a plurality of fibrinogen binding peptides or fibrinogen binding precursor peptides are covalently linked to the carrier.

Preferably X is a hydrophilic group, preferably a straight chain hydrophilic group, more preferably a polyethylene oxide group, suitably of formula —$(CH_2CH_2O)_x$—, where x is at least 1, 2, 4, 6, 8, 10 or 20. Preferably x is up to 50, for example, 1-50, preferably 2-24;

Preferably linker A comprises an —NH— group which forms an amide bond together with the main chain α-carbonyl group of the peptide. Preferably linker A comprises a straight chain group, suitably of formula —$(CH_2)_a$—, wherein a is 1-20, preferably 1-15, 1-10, 1-5, or 2-4. Preferably linker A is covalently linked to spacer group X by an amide bond. Thus, in a preferred arrangement, linker A comprises the following general formula:

—NH—$(CH_2)_a$—NHCO— where a=1-20, preferably 1-15, 1-10, 1-5, or 2-4.

Preferably linker B does not include a disulphide bond. Preferably linker B (and the remainder of the non-peptide spacer) does not include more than one cyclic moiety.

Preferably, linker B comprises a thioether bond. Such bonds are more stable than disulphide bonds.

Use of a maleimide group to crosslink the peptide to the carrier is preferred because it enables formation of a thioether bond by reaction of a maleimide-modified peptide with a thiol group of the carrier. The double bond in the ring of the maleimide group undergoes an alkylation reaction with the thiol group. The reaction can be carried out at neutral pH and is very efficient, releasing only a proton. Thus, use of a maleimide-modified peptide allows the cross-linking reaction to proceed in a single step and use of toxic reagents is avoided. The maleimide group is converted to a succinimide group on reaction, and this succinimide group forms part of the linker.

If desired, thiol groups can be introduced to the carrier for reaction with a maleimide-modified peptide. For example, thiol groups may be added to a carrier that comprises primary amine groups by use of 2-iminothiolane (2-IT). 2-IT is preferred because, on reaction with a maleimide-modified peptide, a straight chain aliphatic linker is generated which links the thiol group to the carrier. Such linker has low immunogenicity.

Thus, in a preferred arrangement, Linker B comprises an aliphatic straight-chain group, preferably with at least four consecutive carbon atoms as part of the straight chain.

It is preferred that linking of the peptide to the carrier does not alter the number of charges on the carrier, since this could adversely affect its solubility. For example, where the carrier comprises a protein, and the peptide is linked to the carrier by reaction with primary amine groups of the carrier (for example, present on lysine residues of the carrier) it is preferred that the non-peptide spacer comprises a positive charge at pH 6-8, preferably physiological pH (pH 7.4), to balance the loss of a positive charge following reaction with the primary amine group. A further advantage of use of 2-IT to add thiol groups to the carrier is that the positively charged imine group of 2-IT is retained after reaction of 2-IT with primary amine groups of the carrier, and on reaction of the resulting thiol group with a maleimide group of a maleimide-modified peptide. Thus, use of 2-IT maintains a positive charge on the carrier and may thereby help maintain its solubility.

In a preferred arrangement, linker B comprises the following general formula:

-succinimide-S—$(CH_2)_b$—Y— where b=2-4, preferably 3; and
Y comprises a group that is positively charged at pH 6-8, preferably pH 7.4. Preferably Y is a group of formula $CNH_2^+$—

More preferably linker B comprises the following general formula:

—$(CH_2)_2$NHCO$(CH_2)_2$-succinimide-S—$(CH_2)_b$—Y—

According to a particularly preferred embodiment of the invention there is provided an agent of the following formula:

[Peptide-CONH—$(CH_2)_2$—NHCO—$(CH_2CH_2O)$—$(CH_2)_2$NHCO$(CH_2)_2$-succinimide-S—$(CH_2)_3$—$CNH_2^+$-]$_n$Carrier     (II)

where x is 2-24; n is >1; and "Peptide-CO" represents a fibrinogen binding peptide or fibrinogen binding precursor peptide and the main chain α-carbonyl group at the carboxy-terminal end of the peptide.

The carrier may be a soluble or insoluble carrier, but is preferably not a platelet. The carrier may be suitable for topical administration to a tissue site of a subject, for example a bleeding wound site, or a mucosal site. Soluble carriers may be suitable for intravenous rather than topical administration. The carrier may comprise a soluble or insoluble protein, a therapeutic drug, a polymer (for example a biocompatible polymer, such as polyethylene glycol), or a combination of any of these. Examples of protein carriers are an enzyme or a protein which is not an enzyme, such as human serum albumin.

An insoluble carrier may be a microparticle (including a solid, hollow, or porous microparticle, preferably a substantially spherical microparticle). The microparticle may be formed of any suitable substance, for example cross-linked protein. A suitable protein is albumin (serum-derived or recombinant, human or non-human in sequence) or gelatin. Microparticles suitable for use as insoluble carriers in the present invention may be formed by spray drying human serum albumin (HSA) using well known spray-drying technology, for example as in WO 92/18164. Alternatives to use of microparticles as carriers include liposomes, synthetic polymer particles (such as polylactic acid, polyglycolic acid and poly(lactic/glycolic) acid), or cell membrane fragments.

At least a majority of the carriers may have a maximum dimension that is less than 6 μm. This may be preferred if the agents of the invention are for intravenous administration.

Alternatively, at least a majority of the carriers may have a maximum dimension that is greater than 6 μm. This may be preferred if the agents of the invention are for topical administration.

In theory there is no upper limit to the number of fibrinogen-binding peptides per carrier molecule. The optimum number is likely to depend on many factors, such as the nature of the carrier, and the number of reactive groups on each carrier for attaching the fibrinogen-binding peptides. However, it is preferred that on average there are up to 100 fibrinogen-binding peptides per carrier molecule. Preferably, on average there are at least three, preferably at least five fibrinogen-binding peptides per carrier molecule. A preferred range is 10-20 fibrinogen-binding peptides per carrier molecule.

The carrier may comprise groups which permit attachment of the non-peptide spacer to the carrier. For example, the carrier may comprise thiol moieties or amine moieties on its surface. If the carrier is proteinaceous, the thiol or amine moieties may be provided by side chains of amino acids, for example cysteine or lysine. Non-peptide groups may be added to the carrier. This is particularly advantageous if the carrier is formed from protein, such as HSA. For example, thiol groups may be added to the carrier using reagents such as 2-iminothiolane (2-IT) which is able to react with primary amine groups on the carrier.

The term "fibrinogen" is used herein to include natural fibrinogen, recombinant fibrinogen, or a derivative of fibrinogen that can be converted by thrombin to form fibrin (for example, natural or recombinant fibrin monomer, or a derivative of fibrin monomer that may or may not be capable of spontaneous assembly). The fibrinogen should be able to bind at least two fibrinogen binding peptides. The fibrinogen may be obtained from any source, and from any species (including bovine fibrinogen), but is preferably human fibrinogen. Human fibrinogen may be obtained from autologous or donor blood. Autologous fibrinogen is preferred because this reduces the risk of infection when biogel of the invention is administered to a subject.

Any suitable fibrinogen binding peptide may be used in agents of the invention. For example, the peptide may be capable of binding to a region of fibrinogen that is naturally bound to fibrin or by the platelet membrane glycoproteins GPIIb-IIIa. Fibrin binding to fibrinogen is discussed in Mosesson et al. 2001, *Ann. N.Y. Acad. Sci.*, 936, 11-30. Binding of GPIIb-IIIa to fibrinogen is discussed in Bennett, 2001, *Annals of NY Acad. Sci.*, 936, 340-354.

The term "peptide" as used herein also incorporates peptide analogues. Several peptide analogues are known to the skilled person. Any suitable analogue may be used provided fibrinogen is able to bind the fibrinogen binding peptide. Fibrinogen binding precursor peptides include peptides which may be converted by a wound site agent to fibrinogen binding peptides or peptide analogues. The term "wound site agent" is used herein to mean an agent which is present at a wound site. In a preferred embodiment the wound site agent is a coagulation factor. Examples of suitable coagulation factors include serine proteases and may be thrombin, Factor VIIa, Factor Xa, or Factor XIa. Preferably the coagulation factor is thrombin.

Examples of suitable fibrinogen binding peptides or fibrinogen binding precursor peptides and how they may be identified are provided in WO 2005/035002, WO 2007/015107 and WO 2008/065388.

Preferably each fibrinogen-binding peptide comprises: an amino acid sequence Gly-Pro-Arg-Xaa (SEQ ID NO: 2) at an amino-terminal end of the peptide, wherein Xaa is any amino acid, preferably any amino acid other than Val, preferably Pro, Sar, or Leu; or an amino acid sequence Gly-His-Arg-Xaa (SEQ ID NO: 3) at an amino-terminal end of the peptide, wherein Xaa is any amino acid, preferably any amino acid other than Pro. A particularly preferred fibrinogen-binding peptide comprises sequence Gly-Pro-Arg-Pro-Gly (SEQ ID NO: 4) at the amino-terminal end.

Preferably the fibrinogen-binding peptides are each 4-60, preferably 4-30, more preferably 4-10, amino acid residues in length.

Preferably the fibrinogen binding peptide binds to fibrinogen with a dissociation constant ($K_D$) of between $10^{-9}$ to $10^{-6}$M, for example around 10, 20, 30, 40, 50, 60, 70, 80, 90, 100, 110, 120, 130, 140, 150, 200, 250, 300, 350, 400, or more nM. A $K_D$ of around 100 nM is preferred. The dissociation constant can be measured at equilibrium. For example, radio-labelled fibrinogen of known concentration can be incubated with microspheres to which the fibrinogen binding moiety has been cross-linked. Typically 5 μM peptide is cross-linked to 1 gm microspheres, or 15-40 μmoles of peptide is cross-linked to 1 gm of microspheres. The peptide-linked microspheres are diluted to 0.5 mg/ml, and incubated in isotonic buffer at pH 7.4 (for example 0.01M Hepes buffer containing 0.15M NaCl) with radio labelled fibrinogen at concentrations of between 0.05 and 0.5 mg/ml for up to 1 hr at 20° C. The fibrinogen bound to the fibrinogen binding moiety on the microspheres can be separated from the free fibrinogen by centrifugation and the amount of free and bound fibrinogen measured. The dissociation constant can then be calculated by Scatchard analysis by plotting concentration of bound fibrinogen against the ratio of the concentrations of bound: free fibrinogen, where the slope of the curve represents $K_D$.

Preferably fibrinogen binds the fibrinogen binding peptide with an affinity that is at least 10 times, more preferably at least 100, 1000, or 10,000 times, the affinity with which fibrinogen binds the fibrinogen binding precursor peptide.

In some embodiments it is preferred that the fibrinogen binding peptide binds selectively to fibrinogen. In other embodiments it is preferred that the fibrinogen binding peptide can bind to fibrinogen, and separately to fibrin monomer and/or fibrin. Binding to fibrinogen and fibrin monomer and/or fibrin is preferably selective.

If the agent comprises a fibrinogen binding precursor peptide, the precursor peptide may comprise a fibrinogen binding peptide joined at its amino terminal end to a sequence that blocks or inhibits (i.e. reduces) binding of fibrinogen to the fibrinogen binding peptide. Cleavage of the fibrinogen binding precursor by a converting agent (preferably a coagulation factor such as thrombin) exposes the fibrinogen binding peptide bound to the carrier, thereby converting the fibrinogen binding precursor to a fibrinogen binding peptide. In such embodiments, the blocking sequence blocks or inhibits the ability of the fibrinogen binding peptide to bind fibrinogen until cleavage occurs. Preferably the blocking sequence is 1-30 amino acid residues in length.

It will be appreciated that in such embodiments the fibrinogen binding precursor should comprise a cleavage site that is recognised specifically by the converting agent and which is located between the fibrinogen binding peptide and the blocking component. Thrombin is a preferred converting agent. However, other serine proteases or coagulation factors may be used to cleave the fibrinogen binding precursor. Thrombin is known to cleave peptide bonds carboxy-terminal to arginine residues, and commonly between arginine and glycine residues.

In particularly preferred embodiments of the invention the fibrinogen binding precursor peptide comprises the amino acid sequence $NH_2$-ZYXR/GPRP- (SEQ ID NO: 5) at its amino terminal end, where "/" represents a thrombin cleavage site, and X is any amino acid, but is preferably proline, Y is any amino acid, but is preferably aspartic acid or alanine, and Z is at least one amino acid that is preferably leucine or proline. Examples are: $NH_2$-LVPR/GPRP- (SEQ ID NO: 6), $NH_2$-ADPR/GPRP- (SEQ ID NO: 7), $NH_2$-LDPR/GPRP- (SEQ ID NO: 8), or $NH_2$-LVPR/GPRV- (SEQ ID NO: 9).

According to the invention, there is also provided a method of producing an agent, which comprises covalently linking a plurality of fibrinogen binding peptides, or fibrinogen binding precursor peptides, to a carrier, so that each peptide is covalently linked to the carrier by a non-peptide spacer attached directly to a main chain α-carbonyl group at a carboxy-terminal end of the peptide.

The plurality of fibrinogen binding peptides or fibrinogen binding precursor peptides may be covalently linked to the carrier by: providing a peptide-spacer conjugate comprising a fibrinogen binding peptide, or fibrinogen binding precursor peptide, covalently linked to a reactive group by a non-peptide spacer group, wherein the non-peptide spacer group is linked to a main chain α-carbonyl group at a carboxy-terminal end of the peptide; and reacting the reactive group of the peptide-spacer conjugate with a reactive group linked to the carrier.

Methods of the invention may further comprise producing the peptide-spacer conjugate for reaction with the carrier. According to a preferred embodiment, the peptide-spacer conjugate is produced by providing a heterobifunctional cross-linking agent comprising a first reactive group linked to a second reactive group by a non-peptide spacer group, and reacting the first reactive group with a reactive group of a non-peptide linker linked directly to the main chain α-carbonyl group at the carboxy-terminal end of the peptide.

The plurality of fibrinogen binding peptides or fibrinogen binding precursor peptides may be covalently linked to the carrier by: providing a heterobifunctional cross-linking agent comprising a first reactive group linked to a second reactive group by a non-peptide spacer group; reacting the first reactive group with a reactive group of a first non-peptide linker linked directly to the main chain α-carbonyl group at the carboxy-terminal end of the peptide; and reacting the second reactive group with a reactive group of a second non-peptide linker linked to the carrier.

Reaction of the first and second reactive groups of the heterobifunctional cross-linking agent may be carried out in any order. According to a preferred embodiment, the first reactive group of the heterobifunctional cross-linking agent is reacted with the reactive group of the first non-peptide linker prior to reaction of the second reactive group of the heterobifunctional cross-linking agent with a reactive group of the second non-peptide linker.

According to a preferred embodiment, the heterobifunctional cross-linker comprises an amine-reactive group and a thiol-reactive group. Preferably the first reactive group of the heterobifunctional cross-linker is an amine-reactive group, and the second reactive group of the heterobifunctional cross-linker is a thiol-reactive group. The amine-reactive group may comprise an activated ester, such as N-hydroxysuccinimide (NHS). The thiol-reactive group may comprise a maleimide group.

Preferably reaction of the first reactive group of the heterobifunctional cross-linker with the reactive group of the first non-peptide linker linked to the peptide forms an amide bond.

Preferably reaction of the second reactive group of the heterobifunctional cross-linker with the reactive group of the second non-peptide linker linked to the carrier forms a thioether bond.

Preferably the non-peptide spacer group, the first non-peptide linker, and the second non-peptide linker, are as defined above.

In preferred embodiments, the peptide is a protected peptide prior to reaction of the first reactive group of the heterobifunctional cross-linking agent with the reactive group of the first non-peptide linker, and is then deprotected following the reaction.

Methods of the invention may further comprise producing a derivatised carrier for reaction with the heterobifunctional cross-linker, which comprises providing the carrier with reactive groups for reaction with the second reactive group of the heterobifunctional cross-linker. The reactive groups may be linked to the carrier by a non-peptide linker. Preferably the non-peptide linker does not include any cyclic groups so as to minimise the immunogenicity of the derivatised carrier. Preferably the non-peptide linker comprises an aliphatic straight chain group, suitably comprising up to four consecutive carbon atoms as part of the straight chain.

In a preferred embodiment, the carrier is provided with reactive groups for reaction with the second reactive group of the heterobifunctional cross-linker by reacting the carrier with a derivatising agent. Preferably the carrier is provided with thiol groups. In a preferred embodiment, the carrier comprises primary amine groups (for example, present on lysine residues of a proteinaceous carrier), and the derivatising agent is 2-iminothiolane (2-IT), which reacts with a primary amine group to expose a thiol group linked to the carrier by a $(CH_2)_3CNH_2^+$— group.

According to the invention, there is also provided a peptide-spacer conjugate for attachment to a carrier, which comprises a fibrinogen binding peptide, or a fibrinogen binding precursor peptide, covalently attached to a non-peptide spacer group, wherein the non-peptide spacer group is covalently linked to a main chain α-carbonyl group at a carboxy-terminal end of the peptide, and a reactive group is attached to the spacer group for reaction with a reactive group of the carrier.

There is also provided a method for producing a peptide-spacer conjugate for attachment to a carrier, which comprises: providing a heterobifunctional cross-linking agent which comprises a first reactive group linked to a second reactive group by a non-peptide spacer group; and reacting the first reactive group with a reactive group of a non-peptide linker covalently linked directly to the main chain α-carbonyl group at the carboxy-terminal end of the peptide.

According to the invention, there is further provided a peptide-linker conjugate for attachment to a non-peptide spacer group, which comprises a fibrinogen binding peptide, or a fibrinogen binding precursor peptide, covalently attached to a non-peptide linker, wherein the non-peptide linker is covalently linked directly to a main chain α-carbonyl group at a carboxy-terminal end of the peptide, and comprises a reactive group for reaction with the spacer group.

There is also provided a method for producing a peptide-linker conjugate for attachment to a non-peptide spacer group, which comprises: providing a fibrinogen binding peptide or fibrinogen binding precursor peptide linked to a solid phase by a non-peptide linker covalently linked directly to the main chain α-carbonyl group at the carboxy-terminal end of the peptide; and releasing the non-peptide linker attached to the peptide from the solid phase to provide a reactive group attached to the peptide by the non-peptide linker.

The peptide is preferably made by a conventional solid-phase peptide synthesis method. In a preferred method, a non-peptide bifunctional cross-linker is provided which comprises first and second reactive groups linked by a non-peptide linking group. One of the reactive groups of the cross-linker is reacted with a reactive group of the resin (for example, a 2-chlorotrityl resin and an ethylenediamine cross-linker may be used). The fibrinogen binding peptide or fibrinogen binding precursor peptide is then synthesised in the carboxy- to amino-direction, beginning with reaction of the carboxylic acid group of the amino acid that will form the carboxy-terminal amino acid of the peptide with the other reactive group of the cross-linker. Once peptide synthesis is complete, the peptide attached to the non-peptide linking group is cleaved from the resin, thereby regenerating a reactive group attached to the non-peptide linking group.

The amino-terminal end of the peptide, and functional groups of the amino acid side chains are protected by protecting groups during synthesis. Suitable protecting groups are known to the skilled person. For example, a suitable protecting group for the amino-terminal end of the peptide is a t-Butoxycarbonyl (t-Boc) group. Suitable protecting groups for the amino acid side chains may depend on the particular side chains present. For example, a fibrinogen binding peptide of amino acid sequence NH$_2$-Gly-Pro-Arg-Pro-Gly- (SEQ ID NO: 4) may include a protecting group for the primary amine group of the arginine side chain. A suitable protecting group for this side chain is 2,2,4,6,7-pentamethyldihydrobenzofurane (Pbf).

The protecting groups preferably remain on the peptide for the reaction of the reactive group of the peptide-linker conjugate with the heterobifunctional cross-linker. The protecting groups are preferably removed before reaction of the reactive group of the peptide-spacer conjugate with the reactive groups of the derivatised carrier.

Figure 2:
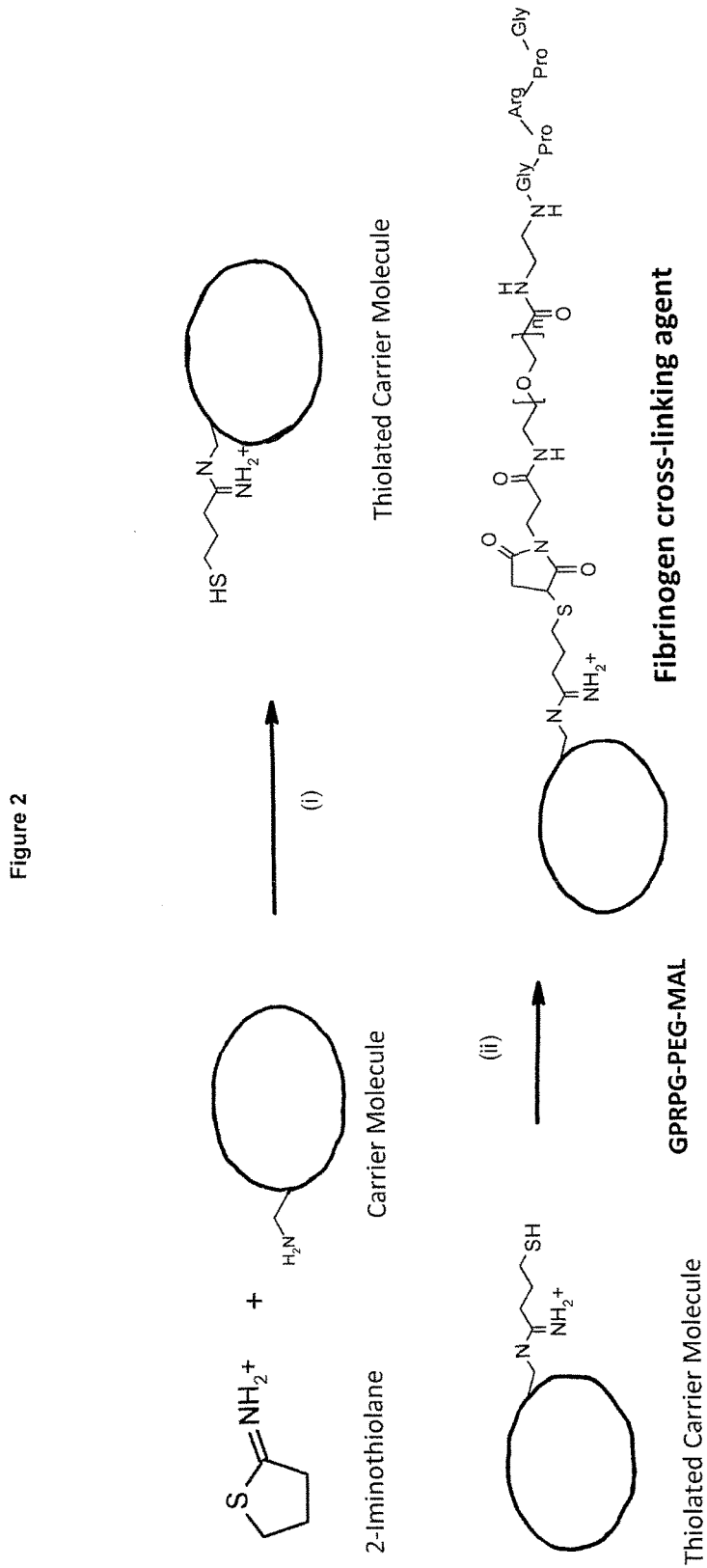

Preferred methods of synthesis of agent of the invention are described in detail in Examples 1 and 4, with reference to FIGS. 1 and 2.

There is also provided according to the invention a fibrinogen binding peptide or fibrinogen binding precursor peptide immobilised to a solid phase by a non-peptide linker, wherein the non-peptide linker is covalently linked directly to a main chain α-carbonyl group at a carboxy-terminal end of the peptide.

There is also provided according to the invention a heterobifunctional cross-linking agent for cross-linking a fibrinogen binding peptide or fibrinogen binding precursor peptide to a carrier, which comprises a thiol-reactive group, an amine-reactive group and a non-peptide spacer group linking the thiol-reactive group to the amine-reactive group, wherein the non-peptide spacer group does not form intramolecular bonds.

The non-peptide spacer group may comprise a hydrophilic group. In a preferred embodiment, the hydrophilic group is a straight chain. The hydrophilic group may comprise an ethylene oxide group such as a polyethylene glycol (PEG) of formula —(CH$_2$CH$_2$O)$_x$—, where x may be 1-50, but is preferably 2-24 or at least 1, 2, 4, 6, 8, 10 or 20. More preferably x is 12. It is advantageous to use a hydrophilic group comprising an ethylene oxide group because it is non-toxic and highly flexible.

The thiol-reactive group of the cross-linking agent preferably comprises a maleimide group. The amine-reactive group may comprise an activated ester, preferably N-hydroxysuccinimide (NHS). Preferably the cross-linking agent comprises both a maleimide group and a NHS group.

According to a preferred arrangement, the heterobifunctional cross-linker has the following general formula:

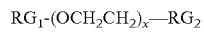

where:
RG$_1$=an amine-reactive group;
RG$_2$=a thiol-reactive group;
x=1-50, preferably 2-24, more preferably 12.

There is also provided according to the invention use of a heterobifunctional cross-linking agent of the invention to immobilise a fibrinogen binding peptide, or a fibrinogen binding precursor peptide, to a carrier.

There is also provided according to the invention a pharmaceutical composition comprising an agent of the invention and a pharmaceutically acceptable carrier, excipient, or diluent.

The agent may be formulated in suspension in an isotonic buffer at physiological pH. A buffer containing mannitol, glucose, human albumin, or trehalose could be used. The agent may be lyophilised to produce a freeze-dried dosage form which can be reconstituted immediately prior to use.

There is also provided according to the invention, an agent of the invention for use as a medicament.

There is also provided according to the invention, use of an agent of the invention in the manufacture of a medicament for preventing, treating, or ameliorating thrombocytopenia or thrombasthenia.

There is also provided according to the invention, an agent of the invention for use in the prevention, treatment, or amelioration of thrombocytopenia or thrombasthenia.

There is further provided according to the invention, a method for preventing, treating, or ameliorating thrombocytopenia or thrombasthenia which comprises administering an agent of the invention to a subject in need of such treatment.

Thrombocytopenia is diagnosed by counting blood cells. The normal platelet count is 150-400×10$^9$/l. Below this range primary haemostasis is impaired and bleeding time prolonged. However, spontaneous life threatening bleeding will usually only occur when the platelet count drops under 10×10$^9$/l. Methods of the invention may be used where the subject has a platelet count below 400×10$^9$/l, preferably below 150×10$^9$/l, more preferably below 10×10$^9$/l.

The most common cause of thrombocytopenia is a failure in platelet production from the bone marrow, such as in blood cancers or following cytotoxic chemotherapy or radiotherapy.

Thrombocytopenia may result from conditions that cause increased platelet destruction. These include Immune thrombocytopenic purpura, disseminated intravascular coagulation, heparin-induced thrombocytopenia, other drug-induced thrombocytopenias, systemic lupus erythematosus, HIV-1-related thrombocytopenia, thrombotic thrombocytopenia purpura/haemolytic-uremic syndrome, common variable immunodeficiency, and post-transfusional purpura. Thrombocytopenia may result from conditions that cause decreased platelet production. These include thrombocytopenia with absent radii (TAR) syndrome, amegakaryocytic thrombocytopenia, giant platelet syndromes (such as Bernard-Soulier syndrome, May-Hegglin anomaly, Fechtner syndrome, Sebastian syndrome, Epstein syndrome, Montreal platelet syndrome), and Wiskott-Aldrich syndrome.

Thrombocytopenia may result from conditions that cause sequestration (for example hypersplenism or Nasabach-Merritt syndrome) or increased platelet destruction and hemodilution (such as extracorporeal perfusion).

Thrombasthenia (acquired platelet function defects) may result from uremia, myeloproliferative disorders (such as essential thrombocythemia, polycythemia vera, chronic myeloid leukaemia, and agnogenicmyeloid metaplasia), acute leukaemias and myelodysplatic syndromes, dysproteinemias, extracorporeal perfusion, acquired von Willebrands disease, acquired storage pool deficiency, antiplatelet antibodies, liver disease.

Thrombasthenia (inherited platelet function defects) may result from platelet adhesion conditions (such as Bernard-Soulier syndrome), agonist receptor conditions (such as integrin α2β1 (collagen receptor) deficiency, P2Y$_{12}$ (ADP receptor) deficiency or thromboxane A$_2$ receptor deficiency), signalling pathway conditions (such as Gαq deficiency, phospholipase C-β2 deficiency, cyclooxygenase deficiency, thromboxane synthetase deficiency, lipoxygenase deficiency or defects in calcium mobilisation), secretion conditions (such as storage pool disease, Hermansky-Pudlak syndrome, Chediak-Higashi syndrome, Gray platelet syndrome, Quebec syndrome and Wiskott-Aldrich syndrome), aggregation conditions (such as Glanzmann thrombasthenia or congenital afibringenemia) and platelet-coagulant protein interaction conditions (such as Scott syndrome).

Methods of the invention may be used to prevent, treat, or ameliorate any of the above conditions.

Methods of the invention may also be used to treat patients who have sustained mechanical damage to their platelets, such as occurs during extra corporeal circulation in coronary bypass surgery and/or haemodialysis.

A suitable total dosage of the agent is expected to be in the range 0.1-5 g protein, or 0.1-5 g protein equivalents of protein-based carrier.

There is also provided, according to the invention, use of an agent of the invention as a platelet substitute.

Agents of the invention may also be used in the formation of a biogel. Methods for biogel formation are described in WO 2008/065388.

Agents of the invention may be applied to a wound to control bleeding. According to the invention there is provided a method of controlling bleeding, which comprises administering an agent of the invention to a subject in need of such treatment.

There is also provided according to the invention an agent of the invention for use in controlling bleeding.

There is further provided according to the invention use of an agent of the invention in the manufacture of a medicament for controlling bleeding.

Agents of the invention may be provided packaged with fibrinogen as part of a kit.

Figure 3:
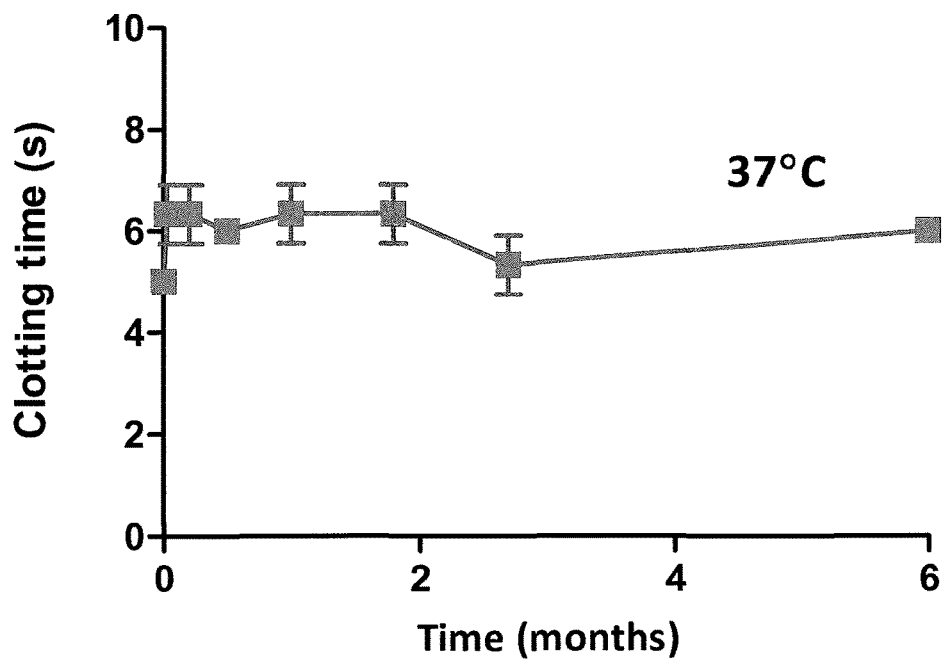

Preferred embodiments of the invention are now described, by way of example only, with reference to the accompanying drawings in which:

FIG. 1 shows a reaction scheme for production of a peptide-spacer conjugate for reaction with a carrier according to a preferred embodiment of the invention:
  i) Ethlyelene diamine
     DIPEA, DCM, 30 min
     Loading Approx. 0.3-0.5 mmol/g;
  ii) Peptide Synthesis;
  iii) Cleavage from the resin, 3% TFA in DCM
     Neutralise immediately with pyridine/MeOH
     Evaporate solvent, purify on C18 column;
  iv) React the protected peptide with NHS-PEG-MAL and DIPEA in DMF:ratio 1:1:2.
     Reaction followed by ESMS when complete mixture acidified/neutralised with formic acid before purification by C18 HPLC;
  v) Freeze dried protected peptide side chain is deprotected in 96% TFA, 2% water, 2% triisopropyl silane for 60 min, solvent is removed by evaporation and purified by C18 HPLC;

FIG. 2 shows a reaction scheme for immobilisation of a fibrinogen binding peptide to a carrier according to a preferred embodiment of the invention:
  i) Reaction 1 h at room temperature, unreacted 2-IT is removed by filtration;
  ii) Reaction 1 h at room temperature, unreacted peptide conjugate is removed by filtration; and FIG. 3 shows the results of stability testing of a preferred embodiment of the invention, comprising fibrinogen-binding peptides immobilised to HSA carrier, in solution stored at 37° C. for 6 months.

A preferred embodiment of an agent of the invention comprises a fibrinogen binding peptide (in this embodiment, the fibrinogen binding peptide has the sequence H$_2$N-Gly-Pro-Arg-Pro-Gly-(SEQ ID NO: 4)) covalently immobilised to a carrier by a non-peptide spacer that is covalently linked directly to a main chain α-carbonyl group at a carboxy-terminal end of the peptide. The agent of the preferred embodiment has the following formula:

[GPRPG-CONH—(CH$_2$)$_2$—NHCO—(CH$_2$CH$_2$O)$_{12}$
—(CH$_2$)$_2$NHCO(CH$_2$)$_2$-succinimide-S—(CH$_2$)$_3$
CNH$_2^+$-]$_n$Carrier where n is >1.

A preferred method for producing an agent of the preferred embodiment is shown in FIGS. 1 and 2, and described below.

Ethylene diamine is reacted with a 2-chlorotrityl resin to produce a resin derivatised with a non-peptide linking group attached to a primary amine group: —NH(CH$_2$)$_2$NH$_2$ (step (i) of FIG. 1).

The peptide is then synthesised starting at the carboxy-terminal end of the peptide. The carboxy-terminal amino acid is joined to the non-peptide linking group of the derivatised resin by reaction of the carboxy group of the amino acid with the primary amine reactive group attached to the linking group. Additional amino acids are then added using a conventional F-moc solid-phase peptide synthesis method (step (ii) of FIG. 1).

The amino-terminal end, and the functional groups of the amino acid side chains of the peptide are protected by protecting groups. In this example, the amino-terminal end is protected with a t-Butoxycarbonyl (t-Boc) group, and the primary amine group of the arginine side chain is protected with a 2,2,4,6,7-pentamethyldihydrobenzofurane (Pbf) group. Other suitable protecting groups will be apparent to the skilled person depending on the particular amino acid residues present.

Once the peptide has been synthesised, it is cleaved from the resin to provide a peptide-linker conjugate comprising a protected peptide with a primary amine group attached to the peptide by a non-peptide linking group (—NH(CH$_2$)$_2$—) linked directly to the main chain α-carbonyl group at the carboxy-terminal end of the peptide (step (iii) of FIG. 1).

This peptide-linker conjugate is then reacted with a heterobifunctional cross-linking agent comprising a thiol-reactive group (a maleimide group) joined to an amine-reactive group (an N-hydroxysuccinmide (NHS) group) by a non-peptide spacer group (a PEG$_n$ spacer). The NHS group of the cross-linker reacts with the primary amine group of the peptide-linker conjugate. The resulting peptide-spacer conjugate comprises a protected peptide attached to a non-peptide spacer group (PEG$_n$) by a non-peptide linker (—NH(CH$_2$)$_2$NHCO—), with a thiol-reactive group (maleimide group) attached to the non-peptide spacer group (step (iv) of FIG. 1). The protected peptide of the peptide-spacer conjugate is then deprotected (step (v) of FIG. 1).

A carrier (a human serum albumin (HSA) carrier) is derivatised with thiol groups using the derivatising agent 2-iminothiolane (2-IT). 2-IT reacts with the primary amine group on the side chain of lysine residues of the carrier to provide the carrier with thiol groups linked to the carrier by a non-peptide linker (—(CH$_2$)$_3$CNH$_2^+$—) (step (i) of FIG. 2). This derivatised carrier is then reacted with the peptide-spacer conjugate to produce the agent of the preferred embodiment (step (ii) of FIG. 2).

A method of synthesis of the agent of the preferred embodiment is described in more detail in Example 4 below, with reference to FIGS. 1 and 2.

Example 1 below describes synthesis of another preferred embodiment in which the peptide-spacer conjugate is reacted with thiol groups of an underivatised carrier. This embodiment has the following structure:

$$[GPRPG\text{-}CONH-(CH_2)_2-NHCO-(CH_2CH_2O)_{12}-(CH_2)_2NHCO(CH_2)_2\text{-succinimide-}]_n\text{Carrier}$$

where n is >1.

EXAMPLE 1

Synthesis of an Agent Comprising a Fibrinogen Binding Peptide Immobilised to a Carrier by a Non-Peptide Spacer Linked Directly to a Main Chain α-Carbonyl Group at a Carboxy-Terminal End of the Peptide Synthesis of a Peptide-Linker Conjugate A 2 chlorotrityl chloride resin is firstly derivatised with ethylenediamine (CAS 107-15-3) (dry DCM, DIPEA), then Fmoc amino acids are coupled in series using standard Fmoc solid phase peptide synthesis techniques to generate the synthetic peptide Gly-Pro-Arg-Pro-Gly (SEQ ID NO: 4) attached to etheylenediamine. The N-terminal glycine amino acid is introduced as the Boc variant.

The side chain, and N-terminally protected peptide is then cleaved from the resin. The peptide is first cleaved using 1% trifluoroacetic acid (TFA) in dichloromethane (DCM) 5×3 mins, then 1.5% TFA, 5×3 mins the fractions pooled and freeze dried. The protected peptide is HPLC purified and freeze dried.

Synthesis of a Peptide-Spacer Conjugate

The free C-terminal amine of the peptide-linker conjugate is reacted with the heterobifunctional cross-linker succinimidyl-[(N-maleimidopropionamido)-dodecaethyleneglycol]ester ($NHS\text{-}PEG_{12}$-Maleimide) (Pierce Co. Product #22112) for 2-3 hours at room temperature in dimethylformamide (DMF) containing 100 ul N,N'-diisopropylethylamine (DIPEA), and the reaction monitored by mass spectrometry. The peptide is reacted in a 1.1 molar excess over the $NHS\text{-}PEG_{12}$-Maleimide. Once the reaction is complete, the product is HPLC purified and freeze dried. Protecting groups are cleaved in 95% (v/v) TFA, 2.5% (v/v) triisopropylsilane, and 2.5% (v/v) water for 1 h at room temperature. The peptide-spacer conjugate is precipitated via the addition of ether, filtered, HPLC purified, and freeze dried to yield the final compound.

Reaction of the Peptide-Spacer Conjugate with the Carrier

The peptide-spacer conjugate is reacted with a carrier comprising spray-dried human serum albumin microparticles for 1 hour at room temperature. Sulfhydryl groups of the carrier react with the maleimide group of the peptide-spacer conjugate to form a stable thioether bond, and thereby immobilise the peptide to the carrier via a non-peptide spacer linked directly to a main chain α-carbonyl group at a carboxy-terminal end of the peptide. Unreacted peptide conjugate is removed by filtration.

The non-peptide spacer group ($PEG_{12}$) has the following advantages: increases the accessibility of the fibrinogen binding peptide to fibrinogen, helps maintain solubility, increases stability, high flexibility, reduced tendency toward aggregation, and reduced immunogenicity.

EXAMPLE 2

Synthesis of an Agent Comprising Fibrinogen Binding Peptide Immobilised to Carrier by a Non-Peptide Spacer Linked to a Lysine Residue at a Carboxy-Terminal End of the Peptide Synthesis of a Peptide with Carboxy-Terminal Lysine The synthetic peptide Gly-Pro-Arg-Pro-Lys (SEQ ID NO: 10) was prepared using standard Fmoc solid-phase peptide synthesis techniques. The N-terminal glycine amino acid is introduced as the Boc variant. The side chain, and N-terminally protected peptide is then cleaved from the resin. The peptide is first cleaved using 1% trifluoroacetic acid (TFA) in dichloromethane (DCM) 5×3 mins, then 1.5% TFA, 5×3 mins the fractions pooled and freeze dried. The protected peptide is HPLC purified and freeze dried.

Synthesis of a Peptide-Spacer Conjugate

The free amine of the C-terminal lysine of the protected peptide is reacted with the heterobifunctional cross-linker succinimidyl-[(N-maleimidopropionamido)-dodecaethyleneglycol]ester ($NHS\text{-}PEG_{12}$-Maleimide) (Pierce Co. Product #22112) for 2-3 hours at room temperature in dimethylformamide (DMF) containing 100 ul N,N'-diisopropylethylamine (DIPEA), and the reaction monitored by mass spectrometry. The peptide is reacted in a 1.1 molar excess over the $NHS\text{-}PEG_{12}$-Maleimide. Once the reaction is complete, the conjugate-protected peptide is HPLC purified and freeze dried. Protecting groups are cleaved in 95% (v/v) TFA, 2.5% (v/v) triisopropylsilane, and 2.5% (v/v) water for 1 h at room temperature. The peptide is precipitated via the addition of ether, filtered, HPLC purified, and freeze dried to yield the final compound.

Reaction of the Peptide-Spacer Conjugate with the Carrier

The peptide-spacer conjugate with the C-terminal lysine was immobilised to carrier in the same way as described in Example 1.

EXAMPLE 3

Fibrinogen Binding Efficiency of Agents with Differently Immobilised Fibrinogen-Binding Peptides The fibrinogen binding efficiency of the agents synthesised as described in Examples 1 and 2 was determined by measuring the amount of fluorescently labeled fibrinogen bound to the different agents by the following method:

5 ml of fibrinogen solution at 20 mg/ml was prepared in 20 mM sodium phosphate buffer pH 7.4 containing 0.15M NaCl to which 5.55 umoles of fluorescein isothiocyanate (FITC) is added in 0.54 ml of dimethyl sulfoxide (DMSO). This reaction was protected from light and incubated at room temperature for 1 h with gentle agitation. To separate the non-conjugated FITC from the FITC-fibrinogen the reaction (5 ml) was loaded on to Sephadex G25 column (XK16) equilibrated 20 mM sodium phosphate buffer, 0.15M NaCl, 1 mM EDTA (pH 7.2). The void fractions containing the fibrinogen were pooled and stored at −20° C. until needed. To determine the F/P ratio (mole/mole) the absorbance of a sample was read by a spectrophotometer at 280 and 495 nm. The calculation for determining the ratio is described by Xia et al, 1996 (Optimally functional fluorescein isothiocyanate-labelled fibrinogen for quantitative studies of binding to activated platelets and platelet aggregation. Br J. Haematol. 1996; 93:204-14). The F/P ratios for the human fibrinogen were typically between 1.5 and 4.

Spray-dried human serum albumin microparticles with immobilized peptide (Example 1) at 0.2 mg/ml protein equivalents were incubated with FITC-fibrinogen (1 mg/ml) for 30 min at room temperature. The reaction was fixed with 0.2% formyl saline and then analyzed by flow cytometry. Microparticles were identified on the basis of their forward and side scatter and their mean fluorescence measured in arbitrary units. The number of fibrinogen molecules bound per particle was calculated from a standard curve of fluorescence reference standard microbeads (Bangs Laboratories, Inc.).

The results of the flow cytometry analysis are shown in Table 1 below:

TABLE I

| Amount of peptide reacted to microparticles (mg) | Number of fibrinogen molecules bound per microparticle | |
|---|---|---|
| | Lysine | Ethylenediamine |
| 1:1 | 5607 | 8317 |
| 2:1 | 6501 | 10103 |

These results show that an agent comprising fibrinogen binding peptide immobilised to carrier by a non-peptide spacer linked directly to the main chain α-carbonyl group at a carboxy-terminal end of the peptide was able to bind more fibrinogen molecules than an agent in which the fibrinogen binding peptide was immobilised by a non-peptide spacer linked to a side chain of a carboxy-terminal lysine residue of the peptide.

EXAMPLE 4

Synthesis of an Agent Comprising Fibrinogen Binding Peptide Immobilised to Derivatised Carrier by a Non-Peptide Spacer Linked Directly to a Main Chain α-Carbonyl Group at a Carboxy-Terminal End of the Peptide Synthesis of a Peptide-Spacer Conjugate A peptide spacer conjugate is synthesised as described in Example 1.

Derivatisation of the Carrier with 2-Iminothiolane (2-IT)

2-IT is used to derivatise the carrier to provide thiol groups for reaction with the maleimide group of the peptide-spacer conjugate. The carrier (formed from HSA in this example), is incubated with 2-IT, which reacts with primary amines on the carrier to introduce sulfhydryl groups. Unreacted 2-IT is removed by filtration.

Reaction of the Peptide-Spacer Conjugate with the Derivatised Carrier

The peptide-spacer conjugate is reacted with the derivatised carrier for 1 hour at room temperature. Sulfhydryl groups of the derivatised carrier react with the maleimide group of the peptide-spacer conjugate to form a stable thioether bond, and thereby immobilised the peptide to the carrier via a non-peptide spacer linked directly to a main chain α-carbonyl group at a carboxy-terminal end of the peptide. Unreacted peptide conjugate is removed by filtration.

The linker between the carrier and the non-peptide spacer group ($—(CH_2)_3CNH_2^{4+}$) is a straight-chain aliphatic group. This has reduced immunogenicity compared with conventional linkages that include a cyclic group. This linker also preserves the original positive charge of the primary amine thereby helping to maintain the solubility of the protein.

EXAMPLE 5

Conjugation of Fibrinogen-Binding Peptide to an Albumin Carrier

This example describes conjugation of a peptide-spacer conjugate of the invention, comprising a fibrinogen-binding peptide of sequence GPRPG (SEQ ID NO: 4) linked to a maleimide group (Mal) by a polyethylene glycol (PEG) linker, to an albumin carrier. The resulting product is referred to as "PeproStat", and is a preferred embodiment of an agent of the invention.

Human serum albumin is diluted to 50 mg/mL in reaction buffer (50 mM sodium phosphate, 150 mM sodium chloride, 100 mM Ethylenediaminetetraacetic acid [EDTA], pH 8.0±0.2) and thiolated by the addition of a sixty-fold molar excess of 2-iminothiolane hydrochloride. After incubation for one hour at room temperature, thiolated albumin is separated from unreacted 2-iminothiolane hydrochloride by tangential flow diafiltration using 20 mM sodium phosphate, 150 mM sodium chloride, 1 mM EDTA pH 7.2±0.2 (filtration buffer).

Peptide conjugation is performed by dissolving peptide (GPRPG-PEG12-maleimide) (SEQ ID NO: 11) at a concentration of 50 mg/mL in filtration buffer and adding to thiolated albumin at a ratio of 0.95 mg peptide per 1 mg albumin. Following incubation for one hour at room temperature, excess peptide is removed by dialysing against a 60-fold excess of Tris-buffered saline (TBS; 20 mM Tris, 150 mM sodium chloride pH 7.2±0.2) using dialysis membrane with a molecular weight cut-off of 10-14 KD for at least 16 hours at 4° C., with one change of buffer. Recovered PeproStat is diluted to 5 mg/mL in TBS, sterile filtered through a 0.2 μm filter, dispensed and stored at 4° C.

The protein content of the final product is estimated by measuring absorbance at 280 nm where E(280, 1%)=5.3.

The activity of the final product is investigated using a Sigma Amelung KC4 coagulometer. Briefly, 30 μL test sample at 0.5 mg/ml is added to 100 μL purified human fibrinogen at 3 mg/ml, the KC4 registers clot formation (i.e. formation of a co-polymer of PeproStat and fibrinogen which has characteristics of a fibrin clot) in less than 6 seconds.

The molecular weight of the final product is estimated by SDS-PAGE of reduced samples using 4-15% Tris-glycine precast gels stained with Coomassie by comparison with the band profile of unstained protein ladder.

Product Profile

| Test | Parameter | Profile |
| --- | --- | --- |
| Adsorption at E280 | Total protein | 5 mg/ml |
| Clotting activity | Activity | 0.5 mg/ml clots in <6 seconds |
| SDS PAGE | Molecular weight | 85-120 KD |

EXAMPLE 6

Haemostatic Properties of Gelatin Carriers with Immobilised Fibrinogen-Binding Peptides This example describes preparation of two different agents of the invention, and their haemostatic properties. Both agents comprise a gelatin carrier, with a plurality of fibrinogen-binding peptides covalently immobilised to the carrier via a PEG linker. To prepare the first agent, 2-iminothiolane was used to covalently attach a plurality of peptide-spacer conjugates of the invention (comprising fibrinogen-binding peptide covalently attached to PEG) to the gelatin carrier. To prepare the second agent, cystamine moieties were conjugated to the carboxyl groups of gelatin in the presence of 1-Ethyl-3-(3-dimethylaminopropyl)carbodiimide hydrochloride (EDC) and N-hydroxysuccinimide (NHS), followed by reductive cleavage of the introduced disulphide bond to generate a free thiol for attachment of the fibrinogen-binding peptide.

Preparation of Gelatin Granules Conjugated with GPRPG-PEG-12-Mal (SEQ ID NO: 11) Using 2-Iminothiolane Gelatin granules were thiolated using 2-iminothiolane which modifies amine residues. The method used was that of Kommareddy S, Amiji M, 2005, *Bioconjugate Chem* 16: 1423-1432.

1 g of gelatin granules were weighed and hydrated in 40 ml of a buffer containing 50 mM sodium phosphate, 0.15M NaCl, 0.1M EDTA pH 8.0±0.2, by mixing on a roller mixer for 10 minutes at room temperature. 102 g of 2-iminothiolane are added to the hydrated gelatin and mixed on a roller mixer for 1 hour. The granules were then spun at 500 rpm-RCF 28 for 2 minutes, the supernatant removed, and volume replaced with 20 mM sodium phosphate, 0.15M NaCl, 0.1 M EDTA pH 7.2±0.2. This was repeated four times to remove the 2-iminothiolane.

An Ellman's assay was performed to measure the number of —SH groups introduced onto the gelatin. Ellman's reagent 5,5'dithiobis(2-nitrobenzoic acid) reacts with sulphydryls under slightly alkaline conditions to release the highly chromogenic compound, 5-thio-2 nitrobenzoic acid (TNB) Ellman GL. (1959) Arch Bichem. Biophys. 82 70-77.

Following quantitation of the —SH groups, 2.5 ml GPRPG-PEG-12-Mal (SEQ ID NO: 11) at 50 mg/ml was added to the granules and roller mixed for 1 hour. The granules were then washed four times with distilled water to remove excess peptide. A slurry of the granules was placed in a plastic container and dried by incubating at 37° C. for 15 hours.

Preparation of Gelatin Granules Conjugated with GPRPG-PEG-12-Mal (SEQ ID NO: 11) Using EDC/Cystamine Chemistry 2.2 g of gelatin granules were weighed out and hydrated in 80 mL of 50 mM MES buffer, pH 6.0, for 15 minutes on a roller mixer. 625 mg of Cystamine, 350 mg of 1-Ethyl-3-(3-dimethylaminopropyl)carbodiimide hydrochloride (EDC), and 130 mg of N-hydroxysuccinimide (NHS) were weighed out and added to hydrated granules. The reaction mixture was left for 2 hours on a roller mixer at ambient temperature, and then split into two 50 mL tubes. The granules were then washed and spun at 500 rpm with 4×40 mL volumes of MES buffer. 200 μL of 1M tris(2-carboxyethyl)phosphine (TCEP) stock was added to each tube and left for 10 minutes on the roller mixer at ambient temperature. A repeat washing with 4 volumes of MES was followed by an Ellman's Assay to determine free SH.

7.2 mL of GPRPG-PEG-12-Mal (SEQ ID NO: 11) at 50 mg/ml was mixed with 10.45 mL of N-ethyl-maleimide and then 8.8 mL of the mixture was added to each tube. The reaction was left for 1 hour on a roller mixer at ambient temperature.

Reactions were washed and spun at 800 rpm with 4 volumes of Milli-Q water to remove excess peptide and N-ethyl-maleimide. Granules were then poured into a plastic box, covered with Nescofilm, the Nescofilm pierced and placed in a bench-top Freeze-Dryer for drying as follows:

Drying Process for Conjugated Granules

The shelves of the freeze-dryer were equilibrated at −36° C., and the gelatin granules placed on the pre-frozen shelf and subjected to thermal treatment steps bringing the temperature up to −20° C. over a period of 270 minutes. Primary drying was accomplished over 800 minutes decreasing the vacuum from 800 mTorr with a concomitant increase in temperature to 20° C. The freeze-dried granules were stored in a desiccator prior to testing.

Testing of Dry Gelatin Granules in a Plug Disintegration Test 100 mg of dry conjugated gelatin granules were packed into a 3 ml syringe, and then 0.5 ml tris-buffered saline (TBS) (0.02M Tris, 0.15M NaCl, pH 7.2±0.2) was added, using a syringe connector, to suspend the granules. 0.5 ml thrombin at 500 u/ml or 0.5 ml TBS was added to 100 mg "blank" (non-conjugated gelatin granules). Using a syringe connector, TBS was passed from another 3 ml syringe into each formulation to suspend it. Each suspension was then mixed by passing it between the syringes approximately 40 times.

The gelatin slurry was added to a third 3 ml syringe and the syringe plunger used to form a plug. 0.2 ml of plasma was then injected into the plug, and left to stand for 3 minutes. The bottom of the syringe was cut off and the plug pushed out into a 50 ml tube containing 0.9% saline. The tube was then mixed on a vortex mixer for up to 10 minutes. The plug was then scored over a period of 10 minutes as follows:

0=plug disintegrated entirely; 2=small lumps present (2-5 mm in size); 5=larger lumps present (5-8 mm); 8=large plug intact, signs of erosion; 10=plug completely intact.

Results

| Sample | Time point (minutes) | Score |
|---|---|---|
| Conjugated granules | 1 | 10 |
|  | 3 | 10 |
|  | 7 | 10 |
|  | 10 | 10 |
| Thrombin/granules | 1 | 10 |
|  | 3 | 10 |
|  | 7 | 10 |
|  | 10 | 10 |
| TBS/granules | 1 | 0 |
|  | 3 | 0 |
|  | 7 | 0 |
|  | 10 | 0 |

The results show that the mechanical durability of the plug formed using the conjugated gelatin granules of the invention is equivalent to that of the non-conjugated granules mixed with thrombin.

EXAMPLE 7

Stability of Fibrinogen-Binding Peptides Immobilised to Carrier in Solution

This example describes the results of stability testing of fibrinogen-binding peptides immobilised to carrier in solution at 37° C.

PeproStat (comprising fibrinogen-binding peptides, each of sequence GPRPG (SEQ ID NO: 4) immobilised to HSA carrier) was stored in solution for 6 months at 37° C. At time zero, and various times during the storage period, samples of the stored solution were assayed for ability to form a co-polymer with fibrinogen, as follows:

Fibrinogen was diluted in 10 mM HEPES, 0.15M NaCl, pH 7.3+/1 0.2 to 6 mg/ml. 25 μl PeproStat at 5 mg/ml was added to 4000 of the diluted fibrinogen, and the time taken for formation of a visual clot comprising a co-polymer of PeproStat and fibrinogen was recorded.

The results are shown in FIG. 3, and demonstrate that PeproStat is stable in solution at 37° C. for at least 6 months.

The invention claimed is:

1. An agent, comprising a carrier and a plurality of peptides that are selected from fibrinogen binding peptides and fibrinogen binding precursor peptides, wherein each peptide is covalently immobilised to the carrier by a non-peptide spacer that is covalently linked directly to a main chain α-carbonyl group at a carboxy-terminal end of the peptide.

2. The agent of claim 1, wherein the non-peptide spacers do not form intramolecular bonds.

3. The agent of claim 1, wherein each non-peptide spacer comprises a hydrophilic group.

4. The agent of claim 3, wherein at least one of:
   (i) the hydrophilic group is at least 17.6 Å in length,
   (ii) the hydrophilic group is a straight chain group,
   (iii) the hydrophilic group comprises an ethylene oxide group,
   (iv) the hydrophilic group comprises an ethylene oxide group that is a polyethylene glycol group of formula $-(CH_2CH_2O)_x-$, where x is 2-24, and
   (v) the hydrophilic group is covalently linked to the main chain α-carbonyl group of the peptide by a straight chain linker.

5. The agent of claim 3, wherein the hydrophilic group is covalently linked to the main chain α-carbonyl group of the peptide by a straight chain linker, and wherein the straight chain linker comprises at least one of (i) a group of formula $-(CH_2)_a-$, wherein a is 1-4, and (ii) a group of formula $-NH-(CH_2)_a-NH-$, wherein a is 1-4.

6. A pharmaceutical composition comprising the agent of claim 1; and a pharmaceutically acceptable carrier, excipient, or diluent.

7. A biogel formed from, or which comprises, the agent of claim 1.

* * * * *